(12) United States Patent
Bollu et al.

(10) Patent No.: US 9,073,817 B2
(45) Date of Patent: Jul. 7, 2015

(54) EFFICIENT PROCESS TO INDUCE ENANTIOSELECTIVITY IN PROCARBONYL COMPOUNDS

(75) Inventors: Ravindra Babu Bollu, Hyderabad (IN); Narasimha Rao Ketavarapu, Hyderabad (IN); Venkata Sunil Kumar Indukuri, Hyderabad (IN); Seeta Ramanjaneyulu Gorantla, Hyderabad (IN); Satyanarayana Chava, Hyderabad (IN)

(73) Assignee: Laurus Labs Private Limited, Hyderabad (Andhra Pradesh) (IN)

( * ) Notice: Subject to any disclaimer, the term of this patent is extended or adjusted under 35 U.S.C. 154(b) by 380 days.

(21) Appl. No.: 13/531,011

(22) Filed: Jun. 22, 2012

(65) Prior Publication Data

US 2012/0264933 A1 Oct. 18, 2012

Related U.S. Application Data

(63) Continuation-in-part of application No. 12/667,985, filed as application No. PCT/IN2008/000476 on Jul. 30, 2008.

(30) Foreign Application Priority Data

Jan. 31, 2008 (IN) .............................. 262/CHE/2008
Nov. 18, 2011 (IN) ............................ 3953/CHE/2011

(51) Int. Cl.
*C07C 209/68* (2006.01)
*C07D 265/18* (2006.01)
*C07F 3/02* (2006.01)

(52) U.S. Cl.
CPC ............ *C07C 209/68* (2013.01); *C07D 265/18* (2013.01); *C07F 3/02* (2013.01)

(58) Field of Classification Search
CPC ..................................................... C07C 209/68
See application file for complete search history.

(56) References Cited

U.S. PATENT DOCUMENTS

| 5,519,021 A | 5/1996 | Young et al. |
| 5,633,405 A | 5/1997 | Thompson et al. |
| 6,015,926 A | 1/2000 | Chen et al. |
| 7,439,400 B2 * | 10/2008 | Jiang et al. ..................... 564/413 |
| 2010/0286408 A1 * | 11/2010 | Satyanarayana et al. ..... 548/403 |

OTHER PUBLICATIONS

Tan et al. Angew. Chem. Int. Ed. 1999, 38, 711-713.*
MSDS for diethylzinc obtained from Akzo Nobel Polymer Chemicals, issued 1999.*
Hornbeck, J. M. Organic Chemistry, 2nd Edition, Thomson Brooks/Cole, 2005.*
Pierce et al. J. Org. Chem. 1998, 63, 8536-8543.*
Dörwald, "Side Reactions in Organic Synthesis: A Guide to Successful Synthesis Design," 2005, Preface, Wiley-VCH Verlag GmbH & Co. KGaA, Weinheim, Germany.
Tan, et al., "A Novel, Highly Enantioselective Ketone Alkynylation Reaction Mediated by Chiral Zinc Aminoalkoxides," Angewandte Chemie International Edition, 1999, pp. 711-713, vol. 38.
Hornbeck, Organic Chemistry, 2nd Edition, 2005, p. 131, Thomson Brooks/Cole.

* cited by examiner

*Primary Examiner* — Matthew Coughlin
(74) *Attorney, Agent, or Firm* — Blank Rome LLP

(57) ABSTRACT

The present invention provides an efficient method to induce the enantioselectivity in procarbonyl compounds using chiral organometallic complexes. The present invention also provides a method for producing chiral organometallic complexes using a chiral additive, achiral additive, a base and a metal salt.

2 Claims, No Drawings

EFFICIENT PROCESS TO INDUCE ENANTIOSELECTIVITY IN PROCARBONYL COMPOUNDS

CROSS-REFERENCE TO RELATED APPLICATIONS

The present application claims the priority of Indian Patent Application No. 3953/CHE/2011, filed Nov. 18, 2011; and is a continuation-in-part (CIP) of U.S. patent application Ser. No. 12/667,985, filed Jan. 6, 2010, which is a national phase of International Patent Application No. PCT/IN2008/000476, filed Jul. 30, 2008, which in turn claims priority to Indian Patent Application No. 262/CHE/2008, filed Jan. 31, 2008; the entire disclosures which are incorporated herein by reference.

RELATED APPLICATION DATA

This application filed in respect of patents of addition U/Sec 54 for the co-pending application numbered 262/CHE/2008 filed on Jan. 31, 2008, and entitled "AN EFFICIENT PROCESS TO INDUCE ENANTIOSELECTIVITY IN PROCARBONYL COMPOUNDS", the contents of which are incorporated by reference herein. The invention described here forth comprises an improvement in the invention claimed in the 262/CHE/2008.

FIELD OF THE INVENTION

The present invention generally relates to cost effective and industrially applicable process to induce enantioselectivity in procarbonyl compounds with improved yields.

The present invention also relates to an improved process for making organometallic complexes, a process for its use in the preparation of pharmaceutically active medicament, for example antiviral agents like (4S)-6-chloro-4-(2-cyclopropylethynyl)-4-(trifluoromethyl)-2,4-dihydro-1H-3,1-benzoxazin-2-one, a potent HIV reverse transcriptase inhibitor (U.S. Pat. No. 5,519,021).

BACKGROUND OF THE INVENTION

Asymmetric addition of organometallic compounds to carbonyls is a useful method for the production of chiral secondary/tertiary-alcohols. Typically for asymmetric synthesis, the active catalyst is generated in situ by the reaction of Lewis acid with chiral ligands. Addition of organometallic reagents to aldehydes and activated ketones has been achieved with excellent enantioselectivity. With inactivated ketones there has been some success, e.g., using salen 1 and camphanosulphonamide ligand 2.

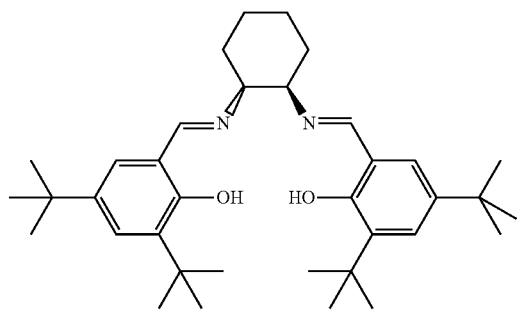

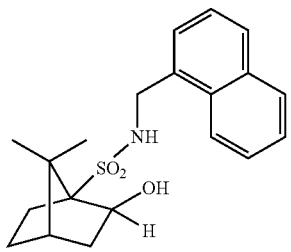

Generally, stoichiometric amount of the promoters [Lewis acid, e.g., $ZnR_2$ (R=alkyl/aryl), $Zn(OTf)_2$, $Cu(OTf)_2$, etc] is required for these asymmetric syntheses. Although, employing these promoters, chiral alcohols has been obtained in high yields and ee upto 99%, they have limited applicability in industrial scale synthesis of the pharmaceutical intermediates, because they are expensive, difficult to store, difficult to handle, especially dialkyl zinc as disclosed in U.S. Pat. No. 5,952,528 ("the '528 patent") and U.S. Pat. No. 6,015,926 ("the '926 patent") are highly pyrophoric and require special modification to transfer the reagent. Moreover the liberated byproducts methane/ethane (when using $ZnMe_2/ZnEt_2$) is a concern on industrial scale synthesis.

The '528 patent and the '926 patent discloses an efficient process for chiral amino alcohol by addition of n-butyl lithium and cyclopropylacetylene to a ketone in presence of a chiral organozinc complex comprising of chiral additive and dialkyl zinc. Alternatively, adding chloromagnesium complex of cyclopropylacetylene to the ketone in presence of the chiral organozinc complex. The synthesis disclosed is schematically represented as follows:

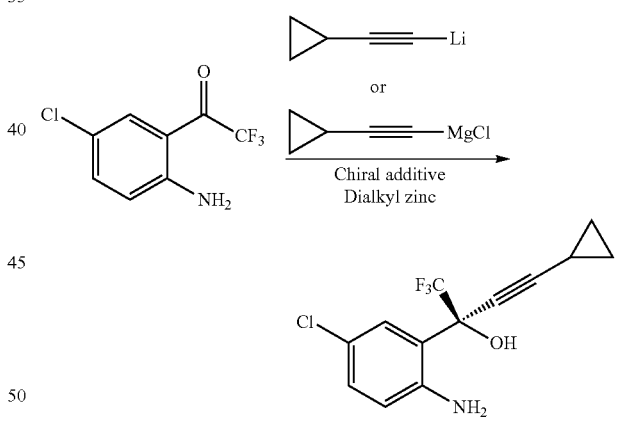

The '926 patent further discloses preparation of chloromagnesium complex of cyclopropylacetylene by reaction of cyclopropylacetylene and Grignard reagent (n-alkyl magnesium chloride). Grignard reactions are highly sensitive to moisture and utmost care to store and use; it requires high volumes of solvent medium for complex formation. This in turn results to utilization of additional manufacturing steps and requires increase in the equipment capacity, particularly on commercial scale.

Patent publication No. WO 2001/70707 ("the '707 publication") discloses an asymmetric process for preparing chiral amino alcohol via chiral ligand mediated asymmetric addition in presence of a large excess of strong lithium base such as n-butyl lithium and LHMDS and excess of chiral moderator.

Patent publication No. WO 96/37457 ("the '457 publication") discloses asymmetric process for preparing chiral amino alcohol by providing a mixture of excess chiral additive with an excess of cyclopropylacetylene and an excess of alkyl lithium followed by mixing it with a ketone at a temperature of about −78° C. to about −20° C.

Although alkyl lithium is frequently used to carry out the aforementioned reaction, it is both expensive and pyrophoric. Thus, alkyl lithium is not an ideal reagent because its use increases costs of production and presents significant safety hazards for users unfamiliar with the handling of pyrophoric materials.

U.S. Pat. No. 7,439,400 ("the '400 patent") discloses a process for the preparation of chiral proparglic alcohol or chiral proparglic amine by first preparing chiral organometallic complex comprising chiral compound, zinc or copper salts such as halides or triflates in presence of organic base such as triethylamine and neat cyclopropylacetylene. The chiral organometallic complex is then mixed with a ketone or ketimine to obtain the chiral proparglic alcohol or chiral proparglic amine. The synthesis disclosed is schematically represented as follows:

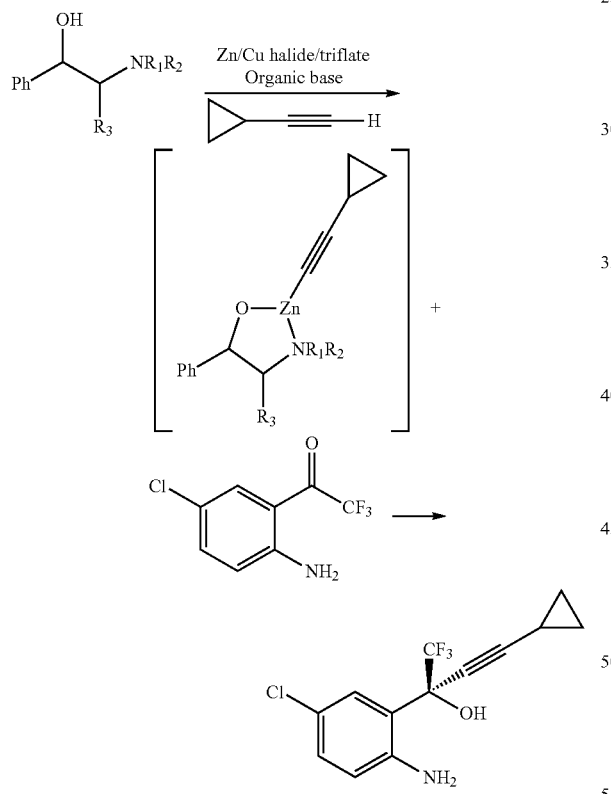

The '400 patent has the following drawbacks, such as:
i) The product, chiral proparglic alcohol or amine obtained are low to moderate yields,
ii) It involves zinc/copper triflates during the formation of chiral zincate complex. These have certain limitations such as a) limited commercial availability, b) expensive reagents, c) difficult to transport, handle and store as these have moisture sensitive, and
iii) Besides this, for use of zinc/copper halides, the nucleophilic displacement of halogens from zinc/copper halides is not feasible with the organic bases.

In view of the limitations associated with the methods of producing chiral amino alcohols, there is a need for an efficient process to induce enantioselectivity in procarbonyl compounds with improved yields without using expensive reagents like n-butyl lithium and dialkyl zinc and avoids precarious Grignard reactions, and a simple, reproducible and straightforward method of producing such a product, which can be carried out using variety of reagents such as inexpensive zinc/copper salts to replacing the expensive and explosive dialkyl zinc for preparing chiral organometallic complex; and using a base and a metal salt for preparing terminal alkyne complex to avoiding the precarious Grignard reactions. The present invention can be practiced on an industrial scale, and also can be carried out without sacrifice of overall yield and enantioselectivity.

Our co-pending Patent application 262/CHE/2008 ("the '262 publication") discloses a process for preparing chiral amino alcohol via preparing an organometallic complex such as organozinc complex comprising the steps of: a) preparing salts of mixture of chiral additive and achiral additive with an inorganic base, b) adding metal halides such as zinc halides to the salts of mixture of chiral additive and achiral additive to obtain the chiral zincate complex, c) adding lithium or magnesium cyclopropylacetylide complex to the chiral zincate complex to obtain chiral organozinc alkyne complex and d) mixing ketone with the chiral organozinc complex. The synthesis disclosed in the '262 publication is schematically represented as follows:

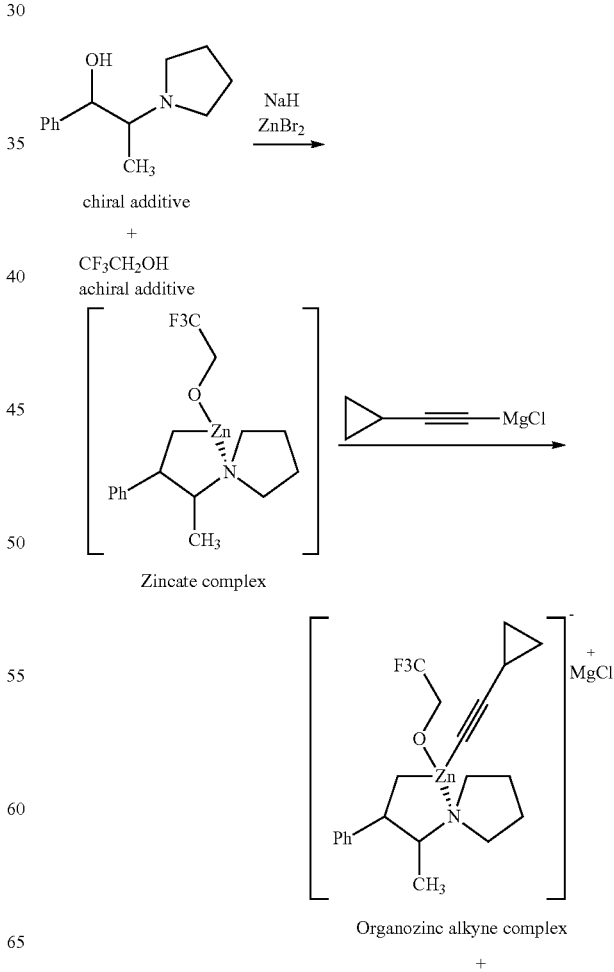

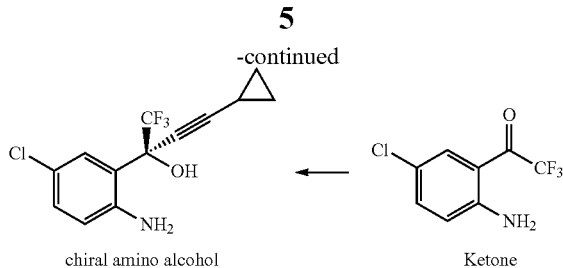

chiral amino alcohol ← Ketone

The advantages associated with the '262 publication include the use of low cost zinc/copper halides are ease of storing, handling and transfer, moreover, the byproducts (sodium salts) formed has no safety concerns.

The present invention has certain improvements over the '262 publication such as use of other zinc/copper salts for forming chiral metal complex and avoids precarious Grignard reactions, therefore usage of large volume of reaction solvent and large capacity of equipment is minimized.

The process of the present invention can be utilized with other active catalysts using chiral additives such as binols, amino alcohols and its derivatives, ethylene diamine and its derivatives in combination with zinc/copper salts.

SUMMARY OF THE INVENTION

The present invention encompasses an efficient method for the preparation of certain organometallic complexes using an active catalyst prepared from at least a chiral additive, an achiral additive, a base, and a metal salt selected from zinc/copper salt; followed by addition of a terminal alkyne complex; and its conversion into alcohols with high enantioselectivity and product yield.

In accordance with one embodiment, the present invention provides a process for the preparation of chiral organometallic complex, comprising the steps of:
a) treating chiral and achiral additive with a base to obtain a salts of chiral additive and achiral additives,
b) adding a zinc/copper salt to obtain a chiral and achiral zinc/copper metal complex, and
c) reacting the chiral and achiral zinc/copper metal complex with a terminal alkyne complex to obtain the chiral organo zinc/copper alkyne complex.

In accordance with a second embodiment, the present invention provides a process for the preparation of chiral organometallic complex, comprising the steps of:
a) treating chiral and achiral additive with a base to obtain a salts of chiral additive and achiral additives,
b) adding a zinc/copper salt to obtain chiral and achiral zinc/copper metal complex,
c) reacting the chiral and achiral zinc/copper metal complexes with a terminal alkyne complex to obtain the chiral organo zinc/copper alkyne complex,
wherein:
the chiral additive is selected from diols, aminoalcohols, ethylenediamines, quinines, camphor sulfonamides, prolines and their derivatives;
the achiral additive is selected from an alcohol (ROH), thiol (RSH), carboxylic acid (RCOOH), sulfonic acid (RSO$_3$H), a hydrogen halide (HX), a carboxamide (RCONH$_2$), and aniline (Ph-NH$_2$), in which R represents $C_{1-6}$ alkyl, $C_{2-6}$ alkenyl, $C_{2-6}$ alkynyl, aryl, where aryl is phenyl or naphthyl, and heteroaryl, where heteroaryl is a 5 or 6-membered aromatic ring substituted with one or two heteroatoms selected from O, S, N; and each of which is unsubstituted or substituted with one, two or three substituents selected from the group consisting of: NO$_2$, Cl, Br, I, F, CF$_3$, $C_{1-6}$ alkyl, $C_{1-6}$ alkoxy, and N[$C_{1-6}$ alkyl]$_2$; and X is F, Cl, Br or I;
the base is selected from the group consisting of metal hydrides, metal hydroxides, metal amides, metal alkoxides, metal carbonates and alkyl lithium compounds; and
the terminal alkyne complex is a compound of formula

R≡≡≡MX wherein R is $C_1$-$C_6$-alkyl, $C_3$-$C_7$-cycloalkyl, $C_1$-$C_6$-alkoxy, aryl, or silyl;
'M' represents a metal cation selected from the group consisting of zinc, magnesium, calcium, strontium and barium and 'X' represents halide such as F, Cl, Br, or I; acetate or sulfate.

In accordance with a third embodiment, the present invention provides a process for the preparation of chiral organometallic complex, comprising the steps of:
a) treating chiral and achiral additive with a base to obtain a salts of chiral additive and achiral additives,
b) adding a zinc/copper salt to obtain chiral and achiral zinc/copper metal complex,
c) reacting the chiral and achiral zinc/copper metal complex with a terminal alkyne complex to obtain the chiral organo zinc/copper alkyne complex,
wherein:
the chiral additive is selected from the group consisting of N-pyrrolidinyl norephedrine and its isomers; N-methylephedrine, ephedrine, N,N-dibenzylnorephedrine, norephedrine, pseudoephedrine and its isomers, N-methylpseudoephedrine and its isomers, diethyl tartrate, pyrrolidinyl pyridine, 2-amino-1,2-diphenylethanol, pyrrolidine-methanol, quinine, quinidine and cinchonine.
the achiral additive is selected from MeOH, EtOH, iPrOH t-BuOH, (CH$_3$)$_3$CCH$_2$OH, (CH$_3$)$_3$CCH(CH$_3$)OH, Ph$_3$COH, Cl$_3$CCH$_2$OH, F$_3$CCH$_2$OH, CH$_2$=CHCH$_2$OH, PhCO$_2$H, PhCH$_2$OH, (CH$_3$)$_2$NCH$_2$CH$_2$OH, 4-NO$_2$-phenol, CH$_3$CO$_2$H, CF$_3$CO$_2$H, and (CH$_3$)CCO$_2$H;
the base is selected from the group consisting of sodium hydride, lithium hydride, sodium amide, potassium amide, sodium dimethyl amide; and
the terminal alkyne complex is a compound of formula

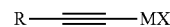

R≡≡≡MX wherein R is $C_3$-$C_7$-cycloalkyl; 'M' represents a metal cation such as magnesium; and 'X' represents Cl or acetate.

In accordance with a fourth embodiment, the present invention provides a process for the preparation of terminal alkyne complex of formula

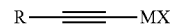

R≡≡≡MX wherein:
wherein R is $C_1$-$C_6$-alkyl, $C_3$-$C_7$-cycloalkyl, $C_1$-$C_6$-alkoxy, aryl, or silyl;
'M' represents a metal cation selected from the group consisting of zinc, magnesium, calcium, strontium and barium and 'X' represents halide such as F, Cl, Br, or I; acetate or sulfate; comprising: reaction of a terminal alkyne compound of formula

with a base and a metal salt MX where M and X are as defined just above.

In accordance with a fifth embodiment, the present invention provides a process for the preparation of a compound of Formula I,

or its enantiomer, wherein $R^1$ is:
a) $C_1$-$C_6$-alkyl, $C_2$-$C_6$-alkenyl, or $C_2$-$C_6$-alkynyl, unsubstituted or mono- or di-substituted with a substituent selected from the group consisting of: halo (Cl, Br, F, I), $CF_3$, CN, $NO_2$, $NH_2$, $NH(C_1$-$C_6$-alkyl), $N(C_1$-$C_6$-alkyl$)_2$, $CONH_2$, $CONH(C_1$-$C_6$-alkyl), $CON(C_1$-$C_6$-alkyl$)_2$, $NHCONH_2$, $NHCONH(C_1$-$C_6$-alkyl), $NHCON(C_1$-$C_6$-alkyl$)_2$, $CO_2$—$C_1$-$C_6$-alkyl, $C_3$-$C_7$-cycloalkyl, or $C_1$-$C_6$-alkoxy; or
b) phenyl, biphenyl, or naphthyl, unsubstituted or substituted with one to four substituents selected from $R^3$, $R^4$, $R^5$, and $R^6$;

$R^3$, $R^4$, $R^5$, and $R^6$ are independently: halo (Cl, Br, F, I), $CF_3$, CN, $NO_2$, $NH_2$, $NH(C_1$-$C_6$-alkyl), $N(C_1$-$C_6$-alkyl$)_2$, $CONH_2$, $CONH(C_1$-$C_6$-alkyl), $CON(C_1$-$C_6$-alkyl$)_2$, $NHCONH_2$, $NHCONH(C_1$-$C_6$-alkyl), $NHCON(C_1$-$C_6$-alkyl$)_2$, aryl, $CO_2$—$C_1$-$C_6$-alkyl, $C_1$-$C_6$-alkyl, $C_2$-$C_6$-alkenyl, $C_2$-$C_6$-alkynyl, $C_3$-$C_7$-cycloalkyl, or $C_1$-$C_6$-alkoxy, such that $C_1$-$C_6$-alkyl is unsubstituted or substituted with aryl, aryl is defined as phenyl, biphenyl, or naphthyl, unsubstituted or substituted with $C_1$-$C_6$-alkyl, $C_1$-$C_6$-alkoxy, $NO_2$, or halo (Cl, Br, F, I);

$R^2$ is: $C_1$-$C_6$-alkyl, $C_2$-$C_6$-alkenyl, or $C_2$-$C_6$-alkynyl, unsubstituted or mono- or di-substituted with a substituent selected from the group consisting of: halo (Cl, Br, F, I), $CF_3$, CN, $NO_2$, $NH_2$, $NH(C_1$-$C_6$-alkyl), $N(C_1$-$C_6$-alkyl$)_2$, $CONH_2$, $CONH(C_1$-$C_6$-alkyl), $CON(C_1$-$C_6$-alkyl$)_2$, $NHCONH_2$, $NHCONH(C_1$-$C_6$-alkyl), $NHCON(C_1$-$C_6$-alkyl$)_2$, $CO_2$—$C_1$-$C_6$-alkyl, $C_3$-$C_7$-cycloalkyl, $C_1$-$C_6$-alkoxy or $C_1$-$C_4$-perfluoroalkyl, and;

$R^7$ is:
$C_1$-$C_6$-alkyl, $C_2$-$C_6$-alkenyl, or $C_2$-$C_6$-alkynyl, unsubstituted or mono- or di-substituted with a substituent selected from the group consisting of: $C_1$-$C_6$-alkyl, $C_3$-$C_7$-cycloalkyl, $C_1$-$C_6$-alkoxy, aryl, or silyl;
comprising reacting a ketone of the formula

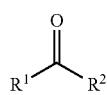

with a chiral organo zinc/copper alkyne complex prepared according to the present invention.

In accordance with a sixth embodiment, the present invention provides a process for the preparation of an amino alcohol of formula:

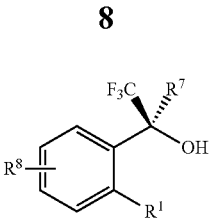

wherein:
$R^1$ is amino or substituted amino,
$R^7$ is:
$C_1$-$C_6$-alkyl, $C_2$-$C_6$-alkenyl, or $C_2$-$C_6$-alkynyl, unsubstituted or mono- or di-substituted with a substituent selected from the group consisting of: $C_1$-$C_6$-alkyl, $C_3$-$C_7$-cycloalkyl, $C_1$-$C_6$-alkoxy, aryl, or silyl; and $R^8$ is halo such as Cl, Br, F or I, comprising the steps of:
a) treating chiral and achiral additive with a base to obtain salts of chiral additive and achiral additives,
b) adding a zinc/copper salt to obtain a chiral and achiral zinc/copper metal complex,
c) reacting the chiral and achiral zinc/copper metal complex with a terminal alkyne complex of formula

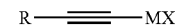

wherein 'R' is $C_1$-$C_6$-alkyl, $C_3$-$C_7$-cycloalkyl, $C_1$-$C_6$-alkoxy, aryl, or silyl; 'M' represents a metal cation selected from the group consisting of zinc, magnesium, calcium, strontium and barium and 'X' represents halide such as F, Cl, Br, or I; acetate or sulfate; to obtain a chiral organo zinc/copper alkyne complex, and d) reacting the resultant chiral organo zinc/copper alkyne complex with a procarbonyl compound of formula

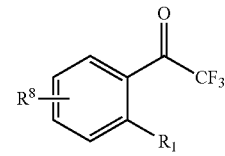

In accordance with a seventh embodiment, the present invention provides a process for the preparation of an amino alcohol of formula

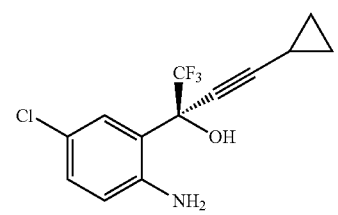

comprising the steps of
a) treating (1R,2S)—N-pyrrolidinyl norephedrine of formula

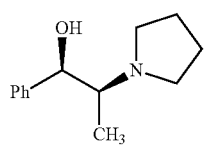

and trifluoroethanol (F$_3$CCH$_2$OH) with sodium hydride to obtain sodium salts of (1R,2S)—N-pyrrolidinyl norephedrine and trifluoroethanol,
b) adding zinc salt selected from chloride, bromide, acetate or sulfate to the resultant sodium salts of (1R,2S)—N-pyrrolidinyl norephedrine and trifluoroethanol to obtain chiral (1R,2S)—N-pyrrolidinyl norephedrine and trifluoroethanol zincate complex of formula,

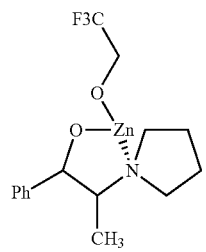

c) mixing the chiral (1R,2S)—N-pyrrolidinyl norephedrine and trifluoroethanol zincate complex with cyclopropylacetylide complex of formula

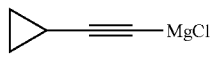

to obtain chiral organozinc complex of formula

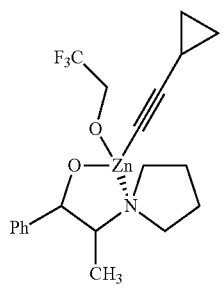

d) mixing the chiral organozinc complex with a ketone of formula

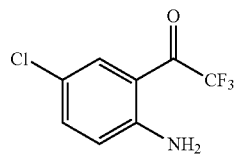

to obtain the amino alcohol product.

DETAILED DESCRIPTION OF THE INVENTION

The present invention encompasses an efficient method for the preparation of organometallic complexes. In particular, the present invention provides an efficient method for the preparation of organometallic complexes without involving the use of dialkyl zinc and precarious Grignard reactions. The present invention further provides a process for preparing alcohols, including amino alcohols, with high enantioselectivity and product yield from the organometallic complexes obtained from the processes of the present invention.

In one embodiment, the present invention provides a process for the preparation of chiral organometallic complex, comprising the steps of:

a) treating chiral and achiral additive with a base to obtain salts of chiral additive and achiral additives, b) adding a zinc/copper salt to obtain a chiral and achiral zinc/copper metal complex, and c) reacting the chiral and achiral zinc/copper metal complex with a terminal alkyne complex to obtain the chiral organo zinc/copper alkyne complex.

In one particular embodiment of the invention, the chiral additive is selected from diols, aminoalcohols, ethylenediamines, quinines, camphor sulfonamides, prolines and their derivatives. The diols and their derivatives are selected from taddol, salen, binols, dimethyl tartrate, diethyl tartrate, diisopropyl tartrate and the like and mixtures thereof;

the aminoalcohols and their derivatives are selected from 2-hydroxy-pyridine derivatives of Formula

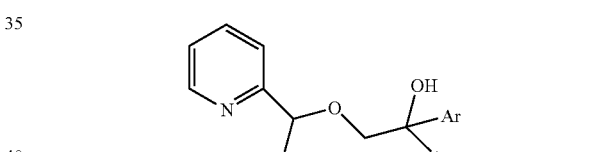

wherein "Ar" is substituted or unsubstituted aryl;
a 2-amino-1,2-diaryl ethanol derivatives of Formula

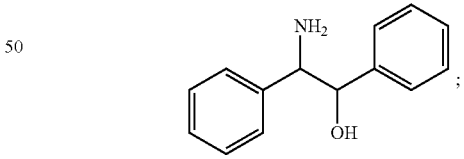

a prolinol derivative of Formula

wherein "P" is H or amino protecting group such as alkyl or benzyl; and an ephedrine derivative of Formula 3,

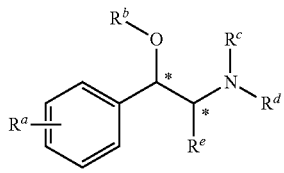

"*" represents chiral centre such as R or S configuration, $R^a$ is H, Halo such as F, Cl, Br, and I; $CH_3SO_3$, $PhCH_2O$, AcO, MeO, EtO, $Me_2NCH_2CH_2O$, $PhCH_2OCO$, $Et_2NCH_2CH_2O$, t-Bu, isopropyl, $NH_2$ or $NO_2$;

$R^b$ is H, alkyl, benzyl or Ac;

one of $R^c$ and $R^d$ is H or amino protecting group such as alkyl or benzyl; or $R^c$ and $R^d$ may combine to form a cyclic ring containing $C_{3-6}$ carbon atoms;

$R^e$ is alkyl such as $C_{1-6}$ alkyl selected from methyl, ethyl, isopropyl, butyl, t-butyl and the like; alkyloxy such as $C_{1-6}$ alkyloxy selected from methyloxy, ethyloxy, propyloxy, isopropyloxy, butyloxy, t-butyloxy and the like; or alkyloxy alkyl, wherein the alkyl represents methyl, ethyl, propyl, isopropyl, butyl, t-butyl, trityl and the like;

the ethylenediamine and their derivatives are selected from piperazine derivative of Formula

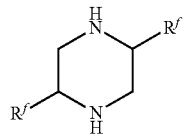

wherein $R^f$ is $C_1-C_4$ alkyl such as methyl, ethyl, isopropyl, t-butyl and the like and halogen such as F, Cl, Br, or I; and a pyrrolidinyl pyridines of Formula

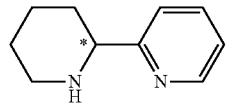

the quinine and their derivatives are selected from cinchonine, quinine or quinidine; the camphor sulfonamides are selected from a compound of Formula

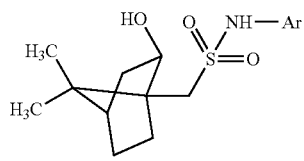

wherein "Ar" is substituted or unsubstituted aryl; and the proline and their derivatives are selected from the compound of Formula

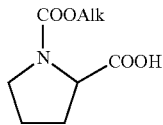

wherein "Alk" represents $C_1-C_4$ alkyl such as methyl, ethyl, isopropyl, t-butyl and the like.

In a preferred embodiment of the invention, the chiral additive is selected from the group consisting of N-pyrrolidinyl norephedrine and its isomers preferably (1R,2S)-isomer; N-methylephedrine, ephedrine, N,N-dibenzylnorephedrine, norephedrine, pseudoephedrine and its isomers preferably (1R,2R) isomer, N-methylpseudoephedrine and its isomers, preferably (1S,2S) isomer, diethyl tartrate, pyrrolidinyl pyridine, 2-amino-1,2-diphenylethanol, pyrrolidine-methanol, quinine, quinidine, and cinchonine. More preferably the chiral additive is (1R,2S)—N-pyrrolidinyl norephedrine.

In one particular embodiment, the achiral additive is selected from an alcohol (ROH), thiol (RSH), carboxylic acid (RCOOH), sulfonic acid ($RSO_3H$), a hydrogen halide (HX), a carboxamide ($RCONH_2$), and aniline ($Ph-NH_2$), in which R represents $C_{1-6}$ alkyl, $C_{2-6}$ alkenyl, $C_{2-6}$ alkynyl, aryl, where aryl is phenyl or naphthyl, and heteroaryl, where heteroaryl is a 5 or 6-membered aromatic ring substituted with one or two heteroatoms selected from O, S, N; and each of which is unsubstituted or substituted with one, two or three substituents selected from the group consisting of: $NO_2$, Cl, Br, I, F, $CF_3$, $C_{1-6}$ alkyl, $C_{1-6}$ alkoxy, and $N[C_{1-6}$ alkyl$]_2$; and X is F, Cl, Br or I.

Preferably the achiral additive is selected from the group consisting of MeOH, EtOH, iPrOH, t-BuOH, $(CH_3)_3CCH_2OH$, $(CH_3)_3CCH(CH_3)OH$, $Ph_3COH$, $Cl_3CCH_2OH$, $F_3CCH_2OH$, $CH_2=CHCH_2OH$, $PhCO_2H$, $PhCH_2OH$, $(CH_3)_2NCH_2CH_2OH$, 4-$NO_2$-phenol, $CH_3CO_2H$, $CF_3CO_2H$, and $(CH_3)CCO_2H$. More preferably the achiral additive is MeOH, iPrOH, t-BuOH or trifluoroethanol ($F_3CCH_2OH$).

The base may conveniently be selected from the group consisting of metal hydrides, metal hydroxides, metal amides, metal alkoxides, metal carbonates and alkyl lithium compounds. The metal hydrides include, but are not limited to, sodium hydride, potassium hydride, lithium hydride and the like; metal hydroxides include, but are not limited to, sodium hydroxide, lithium hydroxide, potassium hydroxide, cesium hydroxide and the like; metal amides include, but are not limited to, alkali metal amides such as lithium amide, sodium amide, potassium amide, cesium amide, rubidium amide and the like, alkyl substituted metal silyl amides such as lithium hexamethyl disilazane (LiHMDS), sodium hexamethyl disilazane (NaHMDS), potassium hexamethyl disilazane (KHMDS) and the like; alkali metal alkyl amides such as sodium methyl amide, sodium dimethyl amide, potassium methyl amide, potassium dimethyl amide, sodium ethyl amide, sodium diethyl amide, potassium ethyl amide, potassium diethyl amide, n-butyl lithium amide and the like; and alkaline earth metal amides such as beryllium amide, magnesium amide, calcium amide, strontium amide, barium amide and the like; metal alkoxides include, but are not limited to, methoxides of lithium, sodium, and potassium; ethoxides of lithium, sodium, and potassium, tertiary butoxides of lithium, sodium, and potassium; metal carbonates include, but are not limited to, sodium carbonate, potassium carbonate, cesium carbonate, lithium carbonate and the like; and alkyl lithium compounds include, but are not limited to $C_{1-6}$ alkyl lithium such as methyl, ethyl, n-propyl, isopropyl, n-butyl, isobutyl, secondary butyl, tertiary butyl, pentyl, isopentyl, n-hexyl and the like.

Preferably the base is selected from the group consisting of sodium hydride, lithium hydride, sodium amide, potassium amide, sodium dimethyl amide. More preferably, the base is sodium hydride or sodium amide.

In a particular embodiment, the zinc/copper salt is selected from its chloride, bromide, iodide, cyanide, benzene sulfonate, toluene sulfonate, methane sulfonate, oxide, acetate, acetylacetonate, citrate, nitrate, phosphate, hydrogenphosphate, dihydrogenphosphate, stearate, sulfate, hydrogen sulfate, carbonate, and bicarbonate. Preferably zinc (II) chloride, bromide, acetate, sulfate; copper (II) chloride, bromide, acetate; more preferably zinc (II) chloride, bromide, acetate or sulfate.

The chiral and achiral zinc/copper metal complex, preferably a zinc complex of chiral additive and achiral additive in the foregoing process may be formed in presence of a solvent. The solvent is selected from a polar or non-polar aprotic solvent, or mixtures thereof. The solvent includes, but is not limited to, tetrahydrofuran (THF), chlorobenzene, o-,m-,p-dichlorobenzene, dichloromethane, toluene, hexane, cyclohexane, pentane, methyl t-butyl ether (MTBE), diethyl ether, N-methylpyrrolidine (NMP), or mixtures thereof; preferably tetrahydrofuran, toluene or mixtures thereof.

Step (c) of the foregoing process may be carried out by treating chiral zinc complex of chiral additive and achiral additive of step b) with a terminal alkyne complex such as a compound of Formula

wherein:
R is $C_1$-$C_6$-alkyl such as methyl, ethyl, isopropyl, t-butyl and the like; $C_3$-$C_7$-cycloalkyl such as cyclopropyl, cyclopentyl, cyclohexyl and the like; $C_1$-$C_6$-alkoxy such as methoxy, ethoxy, propoxy and the like, aryl or silyl; 'M' is a metal cation selected from the group consisting of zinc, magnesium, calcium, strontium and barium; 'X' is a halide such as F, Cl, Br, or I; acetate or sulfate. Preferably "R" is cyclopropyl "M" is magnesium and "X" is Cl; to form a chiral organozinc alkyne complex.

The reaction temperature should be sufficient to effect the formation of chiral organozinc alkyne complex. Typically the reaction temperature may be from about −10° C. to about 50° C. Preferably the reaction temperature is about −5° C. to about 40° C., more preferably at about 0° C. to about 35° C.

The chiral organo zinc/copper alkyne complex recovered using the process of the present invention is a chiral organozinc alkyne complex of formula:

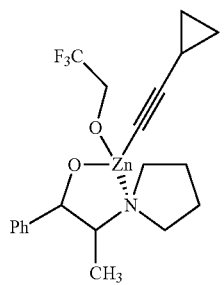

Chiral organozinc alkyne complex when the metal salt is zinc salt, the chiral additive is (1R, 2S)—N-pyrrolidinyl norephedrine and the achiral additive is trifluoroethanol.

In another embodiment, the present invention provides a process for the preparation of terminal alkyne complex of the formula:

wherein:
R is $C_1$-$C_6$-alkyl such as methyl, ethyl, isopropyl, t-butyl and the like; $C_3$-$C_7$-cycloalkyl such as cyclopropyl, cyclopentyl, cyclohexyl and the like; $C_1$-$C_6$-alkoxy such as methoxy, ethoxy, propoxy and the like, aryl or silyl; 'M' is a metal cation selected from the group consisting of zinc, magnesium, calcium, strontium and barium; 'X' is a halide such as F, Cl, Br, or I; acetate or sulfate. Preferably "R" is cyclopropyl, "M" is magnesium and "X" is Cl; comprising reacting a terminal alkyne compound of the formula

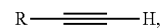

wherein "R" is defined just as above, with a base and a metal salt in an organic solvent to obtain the terminal alkyne complex.

The base in the foregoing process for forming the terminal alkyne complex may be selected from the group consisting of metal hydrides, metal hydroxides, metal amides, metal alkoxides, metal carbonates, lithium compounds, alkaline earth metal alkoxides and amines. The metal hydrides include, but are not limited to sodium hydride, potassium hydride, lithium hydride and the like; metal hydroxides include, but are not limited to sodium hydroxide, lithium hydroxide, potassium hydroxide, cesium hydroxide and the like; metal amides include, but are not limited to alkali metal amides such as lithium amide, sodium amide, potassium amide, cesium amide, rubidium amide and the like; alkyl substituted metal silyl amides such as lithium hexamethyl disilazane (LiHMDS), sodium hexamethyl disilazane (NaHMDS), potassium hexamethyl disilazane (KHMDS) and the like; alkali metal alkyl amides such as sodium methyl amide, sodium dimethyl amide, potassium methyl amide, potassium dimethyl amide, sodium ethyl amide, sodium diethyl amide, potassium ethyl amide, potassium diethyl amide, n-butyl lithium amide and the like; and alkaline earth metal amides such as beryllium amide, magnesium amide, calcium amide, strontium amide, barium amide and the like; metal alkoxides include, but are not limited to methoxides of lithium, sodium, and potassium; ethoxides of lithium, sodium, and potassium; tertiary butoxides of lithium, sodium, and potassium; metal carbonates include, but are not limited to sodium carbonate, lithium carbonate, potassium carbonate, cesium carbonate and the like; lithium compounds include, but are not limited to $C_{1-6}$ alkyl lithium such as methyl, ethyl, n-propyl, isopropyl, n-butyl, isobutyl, secondary butyl, tertiary butyl, pentyl, isopentyl, n-hexyl and the like; alkaline earth metal alkoxides include, but are not limited to magnesium methoxide, magnesium ethoxide, magnesium isopropoxide, magnesium tertiary butoxide and the like; and amines include, but are not limited to dimethyl amine, trimethyl amine, triethyl amine, diisopropyl amine, diisopropyl ethyl amine, piperidine, morpholine, N-methyl morpholine, pyridine, 1,8-diazabicycloundec-7-ene (DBU), 1,4-diazabicyclo[2.2.2]octane (DABCO) and the like. Preferably the base is selected from the group consisting of sodium hydride, lithium hydride, sodium amide, potassium amide, sodium dimethyl amide, magnesium isopropoxide, magnesium tertiary butoxide, lithium tertiary butoxide; more preferably sodium hydride, lithium hydride or sodium amide.

The metal salt in the foregoing process for forming the terminal alkyne complex may be represented by the following formula MX, wherein the 'M' represents a metal cation selected from the group consisting of zinc, beryllium, magnesium, calcium, strontium and barium, preferably magnesium and 'X' represents halide, acetate, sulfate, bisulfate, carbonate, or bicarbonate. The halide includes, but is not limited to F, Br, Cl, I and the like. Preferably, the metal salt is selected from the group consisting of magnesium chloride, magnesium acetate, magnesium sulfate, magnesium bisulfate, magnesium carbonate, magnesium bicarbonate and zinc chloride; and is more preferably magnesium chloride or magnesium acetate.

The organic solvent for forming the terminal alkyne complex may be selected from the group consisting of tetrahydrofuran, chlorobenzene, o-,m-,p-dichlorobenzene, dichloromethane, toluene, hexane, cyclohexane, pentane, methyl t-butyl ether (MTBE), diethyl ether, N-methylpyrrolidine (NMP), or mixtures thereof preferably tetrahydrofuran, toluene or mixtures thereof.

In another embodiment, the present invention provides an alcohol compound of formula I, obtained by a process of the present invention, where the purity of the compound of formula I has an enantiomeric excess equal to or greater than about 99% as determined by HPLC.

In another embodiment, the present invention provides a process for the preparation of a compound of Formula I,

I or its enantiomer, wherein
$R^1$ is: a) $C_1$-$C_6$-alkyl, $C_2$-$C_6$-alkenyl, or $C_2$-$C_6$-alkynyl, unsubstituted or mono- or di-substituted with a substituent selected from the group consisting of: halo (Cl, Br, F, I), $CF_3$, CN, $NO_2$, $NH_2$, $NH(C_1$-$C_6$-alkyl), $N(C_1$-$C_6$-alkyl)$_2$, $CONH_2$, $CONH(C_1$-$C_6$-alkyl), $CON(C_1$-$C_6$-alkyl)$_2$, $NHCONH_2$, $NHCONH(C_1$-$C_6$-alkyl), $NHCON(C_1$-$C_6$-alkyl)$_2$, $CO_2$—$C_1$-$C_6$-alkyl, $C_3$-$C_7$-cycloalkyl, or $C_1$-$C_6$-alkoxy; or
b) phenyl, biphenyl, or naphthyl, unsubstituted or substituted with one to four substituents selected from $R^3$, $R^4$, $R^5$, and $R^6$;
$R^3$, $R^4$, $R^5$, and $R^6$ are independently: halo (Cl, Br, F, I), $CF_3$, CN, $NO_2$, $NH_2$, $NH(C_1$-$C_6$-alkyl), $N(C_1$-$C_6$-alkyl)$_2$, $CONH_2$, $CONH(C_1$-$C_6$-alkyl), $CON(C_1$-$C_6$-alkyl)$_2$, $NHCONH_2$, $NHCONH(C_1$-$C_6$-alkyl), $NHCON(C_1$-$C_6$-alkyl)$_2$, aryl, $CO_2$—$C_1$-$C_6$-alkyl, $C_1$-$C_6$-alkyl, $C_2$-$C_6$-alkenyl, $C_2$-$C_6$-alkynyl, $C_3$-$C_7$-cycloalkyl, or $C_1$-$C_6$-alkoxy, such that $C_1$-$C_6$-alkyl is unsubstituted or substituted with aryl, aryl is defined as phenyl, biphenyl, or naphthyl, unsubstituted or substituted with $C_1$-$C_6$-alkyl, $C_1$-$C_6$-alkoxy, $NO_2$, or halo (Cl, Br, F, I);
$R^2$ is: $C_1$-$C_6$-alkyl, $C_2$-$C_6$-alkenyl, or $C_2$-$C_6$-alkynyl, unsubstituted or mono- or di-substituted with a substituent selected from the group consisting of: halo (Cl, Br, F, I), $CF_3$, CN, $NO_2$, $NH_2$, $NH(C_1$-$C_6$-alkyl), $N(C_1$-$C_6$-alkyl)$_2$, $CONH_2$, $CONH(C_1$-$C_6$-alkyl), $CON(C_1$-$C_6$-alkyl)$_2$, $NHCONH_2$, $NHCONH(C_1$-$C_6$-alkyl), $NHCON(C_1$-$C_6$-alkyl)$_2$, $CO_2$—$C_1$-$C_6$-alkyl, $C_3$-$C_7$-cycloalkyl, $C_1$-$C_6$-alkoxy perfluoroalkyl; and
$R^7$ is:
$C_1$-$C_6$-alkyl, $C_2$-$C_6$-alkenyl, or $C_2$-$C_6$-alkynyl, unsubstituted or mono- or di-substituted with a substituent selected from the group consisting of: $C_1$-$C_6$-alkyl, $C_3$-$C_7$-cycloalkyl, $C_1$-$C_6$-alkoxy, aryl, or silyl;
comprising reacting the chiral organometallic alkyne complex, preferably chiral organozinc alkyne complex obtained by the processes herein described above, with procarbonyl compound of formula

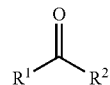

wherein $R^1$ and $R^2$ are as defined in the aforementioned embodiments.

In a preferred embodiment, the compound of formula

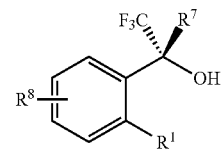

wherein:
$R^1$ is amino or substituted amino, $R^8$ is halo such as Cl, Br, F and I and $R^7$ is defined as above; can be prepared by reacting the chiral organo zinc/copper alkyne complex, preferably chiral organozinc alkyne complex of formula:

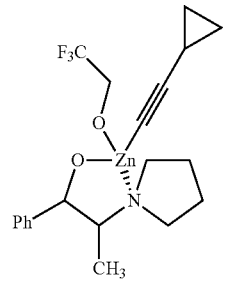

for example, when obtained as described above, with a procarbonyl compound of formula.

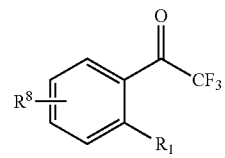

The reaction of the chiral organo zinc alkyne complex and the procarbonyl compound may be carried out in presence of an organic solvent at temperature of about −20° C. to about 60° C., preferably at about 5° C. to about 35° C. The organic solvent includes, but is not limited to, tetrahydrofuran, chlorobenzene, o-,m-,p-dichlorobenzene, dichloromethane, toluene, hexane, cyclohexane, pentane, methyl t-butyl ether (MTBE), diethyl ether, N-methylpyrrolidine (NMP), or mixtures thereof; preferably tetrahydrofuran, toluene or mixtures thereof.

In a further embodiment, the present invention provides a process for the preparation of an amino

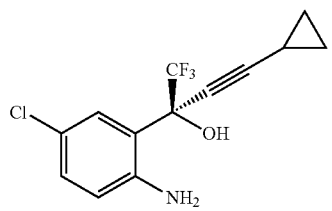 [SMILES: Nc1ccc(Cl)cc1[C@@](O)(C#CC1CC1)C(F)(F)F]

comprising the steps of a) treating (1R,2S)—N-pyrrolidinyl norephedrine of formula

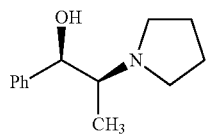

and trifluoroethanol ($F_3CCH_2OH$) with sodium hydride in an organic solvent such as mixture of toluene and THF, at a temperature of about 10° C. to about 80° C., preferably about 25° C. to about 60° C., to obtain sodium salts of (1R,2S)—N-pyrrolidinyl norephedrine and trifluoroethanol, b) adding a zinc salt such as zinc chloride, bromide, acetate or sulfate to the resultant solution containing the sodium salts of (1R,2S)—N-pyrrolidinyl norephedrine and trifluoroethanol to obtain chiral (1R,2S)—N-pyrrolidinyl norephedrine and trifluoroethanol zincate complex of formula:

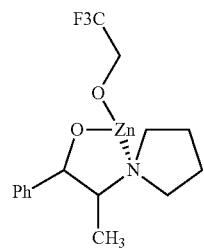

c) mixing the chiral (1R,2S)—N-pyrrolidinyl norephedrine and trifluoroethanol zincate complex with magnesium chloride complex of cyclopropylacetylide of formula:

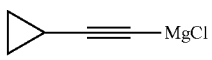

at a temperature of about 0° C. to about 30° C., preferably about 10° C. to about 20° C., to obtain chiral organozinc alkyne complex of formula

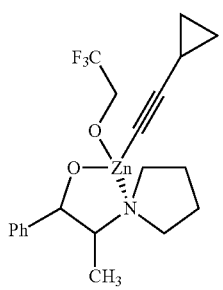

and d) mixing the chiral organozinc alkyne complex with a ketone of formula

at a temperature of about 0° C. to about 30° C., preferably about 10° C. to about 20° C. to obtain the amino alcohol.

The present invention provides an amino alcohol, obtained by the process described herein, having enantiomeric excess of at least about 97%, as measured by HPLC, preferably at least about 98% as measured by HPLC, and more preferably at least about 99%, as measured by HPLC.

The present invention provides an amino alcohol, obtained by the process described herein, as analyzed using the chiral high performance liquid chromatography ("chiral HPLC") with the conditions described below:

Column Chiral: pak AD-H (250×4.6) mm, 5 μm

Flow rate: 1.0 mL/min

Detection wavelength: UV 252 nm

Injection volume: 20 μL

Mode: Isocratic

Diluent: Mobile phase

Column temperature: 30° C.

Mobile phase: n-Hexane, Isopropyl alcohol (90:10)

Sample concentration: 0.5 mg/ml

In a particular embodiment, the present invention provides a method for preparing pharmaceutically active medicaments, for example antiviral agents such as (4S)-6-chloro-4-(2-cyclopropylethynyl)-4-(trifluoromethyl)-2,4-dihydro-1H-3,1-benzoxazin-2-one, also known as DMP-266 (Efavirenz, EFV) with high enantiomeric purity from amino alcohol compound of Formula I, obtained by the process of the present invention. The processes of the invention allow for economical synthesis, shorter reaction times, and yields of high purity. Efavirenz (DMP-266) can be represented by the following structure of formula:

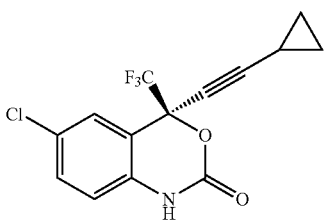

DMP-266

In another embodiment, the present invention provides a process for the preparation of Efavirenz from an amino alcohol compound of Formula I, when obtained by the process described above, by a cyclization reaction, for example using a chloroformate and a base as described in the U.S. Pat. No. '926.

In one preferred embodiment of the present invention, the chiral amino alcohol is prepared according to Scheme I:

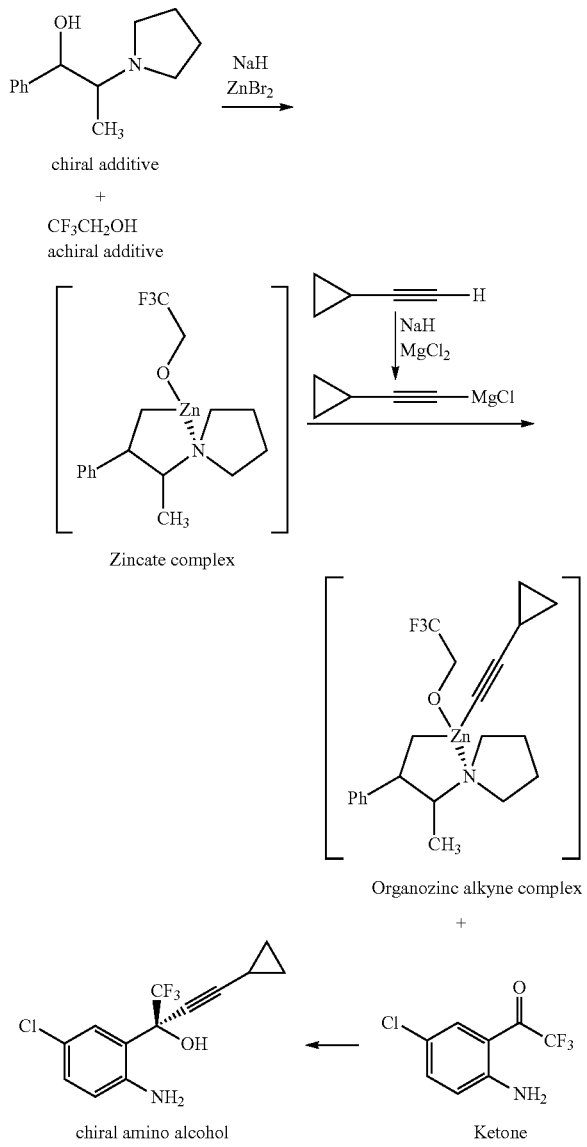

Scheme I

EXAMPLES

The following examples are provided to enable one skilled in the art to practice the invention and are merely illustrative of the invention. The examples should not be read as limiting the scope of the invention as defined in the claims.

Example 1

Preparation of (S)-5-Chloro-α-(cyclopropylethynyl)-2-amino-α-(trifluoromethyl)benzene methanol of Formula

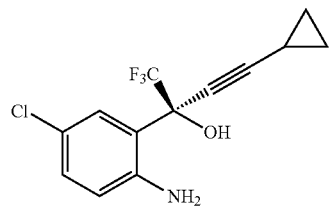 [SMILES: Nc1ccc(Cl)cc1[C@@](O)(C#CC1CC1)C(F)(F)F]

Step A: A solution of chloromagnesium-cyclopropylacetylide (CPA-MgCl) was prepared by adding neat cyclopropyl acetylene (3.62 gms) to a stirred solution of n-butyl magnesium chloride (2M solution in tetrahydrofuran, 26.8 ml) at 0-5° C. The solution was stirred for another 2 hours at 0-5° C. Step B: In another dry flask, to anhydrous tetrahydrofuran (80 ml) at 0-5° C., sodium hydride (57% dispersion in mineral oil, 4.71 gms) was added slowly. The mixture was stirred for 30 minutes at 25° C. to 30° C. and again cooled to 0° C. to 5° C. (1R,2S)-Pyrrolidinyl norephidrine (13.5 gms) and 2,2,2-trifluoroethanol (4.3 gm) were added and stirred for 60 minutes at 25° C. to 30° C. To the reaction mixture, was added a solution of zinc bromide (12 gms) in tetrahydrofuran (40 ml) and stirred for 60 minutes at 25° C. to 30° C., to obtain ephedrine zincate complex. The solution of chloromagnesium-cyclopropylacetylide of Step A was then added to the ephedrine zincate complex at 25° C. to 30° C. and stirred for 2 hours at the same temperature. To the resultant reaction mass was added 4-chloro-2-trifluoroacetyl aniline (10 gms) at 25° C. to 30° C. and the mixture was stirred 15 hours at same temperature. After completion of the reaction, the reaction mixture was quenched with 30% aqueous potassium carbonate (5.5 ml) and the solid precipitate was filtered. The filtrate was taken and partially concentrated and then toluene (100 ml) added followed by washed with 30% citric acid solution in water (50 ml). The organic layer was partially concentrated and hexane (50 ml) was added. The mixture was cooled to 0° C., filtered and the solid precipitate was washed with chilled hexane (10 ml). The wet product was dried at 50° C. to 55° C. under reduced pressure to afford the title compound. Yield: 10 gms.

Example 2

Preparation of (S)-5-Chloro-α-(cyclopropylethynyl)-2-amino-α-(trifluoromethyl)benzene methanol (Using Zinc Chloride for Zincate Complex and Sodium Hydride and Magnesium Chloride for CPA-MgCl Complex)

Step A: Preparation of Chloromagnesium Complex of Cyclopropylacetylide:

In a 1 liter 4 necked round bottom flask was charged tetrahydrofuran (130 ml) and sodium hydride (27.2 gms) at 25° C. to 35° C. The mixture was cooled to 0° C. to 5° C. and a tetrahydrofuran solution of cyclopropyl acetylene (32.4 gms in 34 ml tetrahydrofuran) was added. The mixture was heated to 60° C. to 65° C. and stirred for 2 hours at same temperature. The mixture was then cooled to 25° C. to 35° C. and charged magnesium chloride (51.5 gms). The resulting mixture was stirred at 60° C. to 65° C. for 2 hours and then cooled to 25° C. to 35° C. to obtain the chloromagnesium complex of cyclopropylacetylide.

Step B: A 1 liter 4 necked round bottom flask was charged with tetrahydrofuran (200 ml), (1R,2S)-pyrrolidinyl norephidrine (133.1 gms) and 2,2,2-trifluoroethanol (32.4 gms) at 25° C. to 35° C. to obtain a (1R,2S)-pyrrolidinyl norephidrine and 2,2,2-trifluoroethanol solution.

Step C: A 2 liter 4 necked round bottom flask was charged with tetrahydrofuran (300 ml) and zinc chloride (64 gms) at 25° C. to 35° C. and then slowly charged with sodium hydride (41.3 gms) at same temperature under nitrogen atmosphere. The mixture was stirred for 1 hour at the same temperature and cooled to 10° C. to 15° C. To the reaction mixture, (1R,2S)-pyrrolidinyl norephidrine and 2,2,2-trifluoroethanol solution of Step B and solution of chloromagnesium complex of cyclopropylacetylide of Step A was added at 10° C. to 15° C. The mixture was stirred for 2 hours at the same temperature and a toluene/tetrahydrofuran solution of 4-chloro-2-trifluoroacetyl aniline (100 gms in 150 ml toluene and 100 ml tetrahydrofuran) was at 10° C. to 15° C. Stirring was continued for 2 hours at the same temperature and then mixture was heated to 20° C. to 30° C. Stirring was continued for 2 hours at the same temperature and after completion of the reaction, monitored by HPLC, the mixture was charged with toluene (300 ml) and the reaction mass quenched in a citric acid solution (850 ml) at below 25° C. The resultant mixture was heated to 35° C. to 40° C., the organic layer was separated and concentrated under vacuum at below 45° C. To the residue, was added methanol (300 ml) and the methanol containing product was separated from the oil layer. Water (450 ml) was added to the methanol layer at 10° C. to 15° C. and stirred for 2 hours at same temperature. The precipitated product was filtered and dried at 50° C. to 55° C. under vacuum for 10 hours to afford the title compound as a crude product. The crude compound was recrystallized from toluene to afford the pure compound.

Yield: 115 gms.
Enantiomeric Purity (e.e): 99.7%

Example 3

Preparation of (S)-5-Chloro-α-(cyclopropylethynyl)-2-amino-α-(trifluoromethyl)benzene methanol (Using Zinc Acetate for Zincate Complex and Sodium Hydride and Magnesium Chloride for CPA-MgCl Complex)

Step A: Preparation of Chloromagnesium Complex of Cyclopropylacetylide:

In a 1 liter 4 necked round bottom flask was charged tetrahydrofuran (130 ml) and sodium hydride (27.2 gms) at 25° C. to 35° C. The mixture was cooled to 0° C. to 5° C. and a tetrahydrofuran solution of cyclopropyl acetylene (32.4 gms in 34 ml tetrahydrofuran) was added. The mixture was heated to 60° C. to 65° C. and stirred for 2 hours at same temperature. The mixture was then cooled to 25° C. to 35° C. and charged with magnesium chloride (51.5 gms). The mixture was stirred at 60° C. to 65° C. for 2 hours and then cooled to 25° C. to 35° C. to obtain the chloromagnesium complex of cyclopropylacetylide.

Step B: In a 1 liter 4 necked round bottom flask was charged tetrahydrofuran (200 ml), (1R,2S)-pyrrolidinyl norephidrine (133.1 gms) and 2,2,2-trifluoroethanol (32.4 gms) at 25° C. to 35° C. to obtain a (1R,2S)-pyrrolidinyl norephidrine and 2,2,2-trifluoroethanol solution.

Step C: In a 2 liter 4 necked round bottom flask, was charged tetrahydrofuran (300 ml) and zinc acetate (84 gms) at 25° C. to 35° C. and slowly sodium hydride (41.3 gms) was added at the same temperature under nitrogen atmosphere. The mixture was stirred for 1 hour at the same temperature and cooled to 10° C. to 15° C. To the reaction mixture, (1R,2S)-pyrrolidinyl norephidrine and 2,2,2-trifluoroethanol solution of step B and solution of chloromagnesium complex of cyclopropylacetylide of step A was added at 10° C. to 15° C. The mixture was stirred for 2 hours at the same temperature and a toluene/tetrahydrofuran solution of 4-chloro-2-trifluoroacetyl aniline (100 gms in 150 ml toluene and 100 ml tetrahydrofuran) was added at 10° C. to 15° C. Stirring was continued for 2 hours at the same temperature and then the mixture was heated to 20° C. to 30° C. Stirring was continued for 2 hours at the same temperature and after completion of the reaction, monitored by HPLC, toluene (300 ml) was added and the reaction mass was quenched in citric acid solution (850 ml) at below 25° C. The mixture was heated to 35° C. to 40° C. and the organic layer was separated and concentrated under vacuum at below 45° C. To the residue was added methanol (300 ml) and the methanol containing product was separated from the oil layer. Water (450 ml) was added to the methanol layer at 10° C. to 15° C. and the mixture stirred for 2 hours at the same temperature. The precipitated product was filtered and dried at 50° C. to 55° C. under vacuum for 10 hours to afford the title compound as a crude product. The crude compound was recrystallized from toluene to afford the pure compound.

Yield: 110 gms.
Enantiomeric Purity (e.e): 99.8%

Example 4

Preparation of (S)-5-Chloro-α-(cyclopropylethynyl)-2-amino-α-(trifluoromethyl)benzene methanol (Using Zinc Acetate for Zincate Complex and N-Butyl Magnesium Chloride for CPA-MgCl Complex)

Step A:
A solution of chloromagnesium-cyclopropylacetylide (CPA-MgCl) was prepared by adding neat cyclopropyl acetylene (32.4 gms) to a stirred solution of n-butyl magnesium chloride (2M solution in tetrahydrofuran, 250 ml) at 0-5° C. The solution was stirred for another 2 hours at 0-5° C.

Step B:
In a 1 liter 4 necked round bottom flask was charged tetrahydrofuran (200 ml), (1R,2S)-pyrrolidinyl norephidrine (133.1 gms) and 2,2,2-trifluoroethanol (32.4 gms) at 25° C. to 35° C. to obtain a (1R,2S)-pyrrolidinyl norephidrine and 2,2,2-trifluoroethanol solution.

Step C:
In a 2 liter 4 necked round bottom flask, was charged tetrahydrofuran (300 ml) and zinc acetate (84 gms) at 25° C. to 35° C. and slowly sodium hydride (41.3 gms) was added at the same temperature under nitrogen atmosphere. The mixture was stirred for 1 hour at the same temperature and cooled to 10° C. to 15° C. To the reaction mixture, (1R,2S)-pyrrolidinyl norephidrine and 2,2,2-trifluoroethanol solution of step B and solution of chloromagnesium complex of cyclopropylacetylide of step A was added at 10° C. to 15° C. The mixture was stirred for 2 hours at the same temperature and a toluene/tetrahydrofuran solution of 4-chloro-2-trifluoroacetyl aniline (100 gms in 150 ml toluene and 100 ml tetrahydrofuran) was added at 10° C. to 15° C. Stirring was continued for 2 hours at the same temperature and the mixture was then heated to 20° C. to 30° C. Stirring was continued for 2 hours at the same temperature and after completion of the reaction, monitored by HPLC, toluene (300 ml) was added and the reaction mass was quenched in citric acid solution (850 ml) at below 25° C. The mixture was heated to 35° C. to 40° C. and the organic layer was separated and concentrated under vacuum at below 45° C. To the residue was added methanol (300 ml) and the methanol containing product was then separated from the oil layer. Water (450 ml) was added to the methanol layer at 10° C. to 15° C. and the mixture was stirred for 2 hours at same temperature. The precipitated product was filtered and dried at 50° C. to 55° C. under vacuum for 10 hours to afford the title compound as a crude product. The crude compound was recrystallized from toluene to afford the pure compound.

Yield: 105 gms.
Enantiomeric Purity (e.e): 99.9%

Example 5-8

Preparation of (S)-5-Chloro-α-(cyclopropylethynyl)-2-amino-α-(trifluoromethyl)benzene methanol (with Different Achiral Additives), Using a Procedure Analogous to that Employed in Example 2, as Described in the Following Table I

| Ex | chiral additive | achiral additive | Metal salt | Purity (e.e) |
|---|---|---|---|---|
| 5 | (1R,2S)-pyrrolidinyl norephidrine | Methanol | zinc chloride | 99.8% |
| 6 | (1R,2S)-pyrrolidinyl norephidrine | Ethanol | zinc chloride | 99.7% |
| 7 | (1R,2S)-pyrrolidinyl norephidrine | Isopropanol | zinc chloride | 99.9% |
| 8 | (1R,2S)-pyrrolidinyl norephidrine | t-Butanol | zinc chloride | 99.7% |

Example 9

Preparation of (4S)-6-chloro-4-(2-cyclopropylethynyl)-4-(trifluoromethyl)-2,4-dihydro-1H-3,1-benzoxazin-2-one (DMP-266)

In a 2 liter 4 necked round bottom flask, was charged toluene (300 ml), amino alcohol (100 gms, obtained from Example 3) and potassium carbonate solution (119 gms of potassium carbonate dissolved in 500 ml of water) at 25° C. to 35° C. Triphosgene solution (43 gms of triphosgene in 200 ml toluene) was added at 20° C. to 25° C. and the mixture was stirred for 1 hour at the same temperature. After completion of the reaction, monitored by HPLC, the organic layer was separated and washed with ammonia solution. The organic layer was concentrated under vacuum below 45° C. and methanol (350 ml) was added to the resultant residue. Water (800 ml) was added to the resultant methanol solution and the mixture was stirred at 15° C. to 25° C. for 2 hours. The precipitated material was filtered and washed with water (200 ml). The wet product material was dried at 85° C. to 90° C. under vacuum for about 15 hours to afford the title compound.

Yield: 95 gms.
Enantiomeric Purity (e.e): 99.8%

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

We claim:
1. A process for the preparation of an amino alcohol of formula

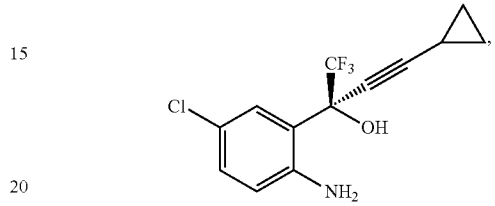

comprising the steps of
a) treating (1R,2S)—N-pyrrolidinyl norephedrine of formula

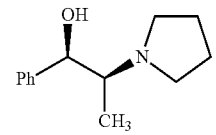

and trifluoroethanol ($F_3CCH_2OH$) with sodium hydride to obtain a sodium salt of (1R,2S)—N-pyrrolidinyl norephedrine and trifluoroethanol,
b) adding a zinc salt to the resultant sodium salts of (1R,2S)—N-pyrrolidinyl norephedrine and trifluoroethanol to obtain chiral (1R,2S)—N-pyrrolidinyl norephedrine and trifluoroethanol zincate complex of formula,

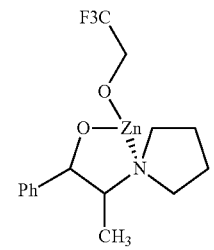

c) reacting a terminal alkyne compound of formula

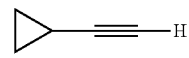

with sodium hydride and $MgCl_2$ to give a cyclopropylacetylide complex of formula

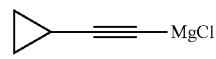

d) mixing the chiral (1R,2S)—N-pyrrolidinyl norephedrine and trifluoroethanol zincate complex with the cyclopropylacetylide complex of formula

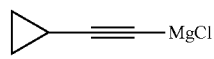

to obtain chiral organozinc complex of formula

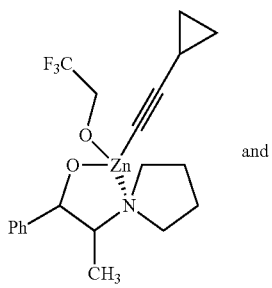

and e) mixing the chiral organozinc complex with a ketone of formula

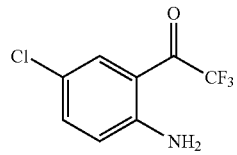 [SMILES: Nc1ccc(Cl)cc1C(=O)C(F)(F)F]

to obtain the amino alcohol.

2. The process of claim 1, wherein the zinc salt is zinc chloride, zinc bromide, zinc acetate, or zinc sulfate.

* * * * *